United States Patent [19]

Chihara et al.

[11] Patent Number: 5,505,771
[45] Date of Patent: Apr. 9, 1996

[54] DENTAL GYPSUM COMPOSITION

[75] Inventors: Shoichi Chihara; Kouichi Morita; Noboru Yamaguchi, all of Mie, Japan

[73] Assignee: Mitsubishi Chemical Corporation, Tokyo, Japan

[21] Appl. No.: 308,209

[22] Filed: Sep. 19, 1994

Related U.S. Application Data

[63] Continuation of Ser. No. 912,183, Jul. 13, 1992, abandoned.

[30] Foreign Application Priority Data

Jul. 17, 1991 [JP] Japan ................................ 3-201203

[51] Int. Cl.$^6$ ...................................................... A61K 6/10
[52] U.S. Cl. ........................ 106/35; 106/38.51; 106/38.7; 106/779
[58] Field of Search ................................. 106/35, 38.51, 106/38.7, 779

[56] References Cited

U.S. PATENT DOCUMENTS

| | | | |
|---|---|---|---|
| 3,926,650 | 12/1975 | Lange et al. | 106/678 |
| 4,647,311 | 3/1987 | Ohi et al. | 106/35 |
| 4,911,759 | 3/1990 | Ohi et al. | 106/111 |

*Primary Examiner*—Margaret Einsmann
*Attorney, Agent, or Firm*—Oblon, Spivak, McClelland, Maier & Neustadt

[57] ABSTRACT

A dental gypsum composition is disclosed, comprising (A) 100 parts by weight of calcined gypsum, (B) from 0.005 to 5.0 parts by weight of an alkali metal tartrate, (C) from 0.1 to 5.0 parts by weight of a sugar alcohol, and (D) from 0.005 to 3.0 parts by weight of a retarder. The composition provides a denture model excellent in surface smoothness, dimensional precision, and mechanical strength even when combined with an impression made of an agar-based material or an alginate-based material.

8 Claims, No Drawings

DENTAL GYPSUM COMPOSITION

This application is a continuation of application Ser. No. 07/912,183, filed on Jul. 13, 1992, now abandoned.

FIELD OF THE INVENTION

This invention relates to a gypsum composition for dental use. More particularly, it relates to a dental gypsum composition mainly comprising calcined gypsum which provides a gypsum model having a smooth surface even when combined with various impression materials, particularly agar-based materials.

BACKGROUND OF THE INVENTION

Calcined gypsum has hydraulic properties (setting on reacting with water) and is thereby used as a model material in various fields. In particular, it is inevitable as a denture model material for preparation of various dental prostheses that are fitted into the oral cavity, such as a full denture, a denture, a crown, a bridge, an inlay, and an occluding frame.

A denture model is generally prepared by making a negative mold called an impression using an impression material, and pouring a slurry of calcined gypsum in water into the mold, followed by setting. Known impression materials include rubbers, e.g., silicone rubbers, polyether rubbers, and polysulfite rubbers; and aqueous colloids, e.g., agar and alginates.

The denture model materials are required to have (1) dimensional precision, (2) mechanical strength, (3) capability of forming a smooth surface in contact with various impression materials, (4) easy handling, (5) stability with time, and (6) easy processing, and (7) to undergo no appreciable foaming.

In order to improve dimensional precision, it is generally necessary to control expansion of gypsum on setting by addition of an expansion inhibitor, such as sulfates, tartrates, and oxalates as disclosed, e.g., in JP-A-50-161492 (the term "JP-A" as used herein means an "unexamined published Japanese patent application"). In order to obtain a high-strength, high-hardness and smooth-surfaced gypsum model, it is known to add to α-type calcined gypsum a metal sulfate and a melamine-formaldehyde resin as disclosed, e.g., in JP-A-62-270451.

While aqueous colloidal impression materials, such as agar and alginates, are disadvantageous in that gypsum models patterned thereon have poor surface smoothness, a composite material composed of agar and an alginate have recently been developed, by which both merits of agar and easy handling and good economy of alginates can be taken advantage of, and has now found frequent clinical use.

However, agar-based impression materials, though excellent in affinity for oral tissues, still involve several problems that need to be addressed in terms of compatibility with gypsum and dimensional stability. That is, gypsum models received from an agar impression sometimes suffer from considerable surface roughness depending on the combination of an agar impression material and a gypsum model material.

For example, JP-A-62-270451 supra states that a gypsum model having a smooth surface can be obtained even when combined with an aqueous colloidal impression material but, in fact, cases are met in which the resulting gypsum model suffers from considerable surface roughening when combined with some impression materials other than specific ones, for example, when combined with an agar impression material. Therefore, a complete solution has not yet been reached. It has thus been demanded to develop a gypsum composition which provides a gypsum model having a smooth surface with dimensional precision without any limitation of an impression material to be combined with.

SUMMARY OF THE INVENTION

An object of the present invention is to provide a dental gypsum composition which provides a gypsum model having a smooth surface with dimensional precision without a limitation of an impression material to be combined with.

The inventors have conducted extensive investigations assuming that control on setting characteristics of a gypsum composition at the portion near the surface in contact with an impression should be important for accomplishment of the above object.

The present invention relates to a dental gypsum composition comprising (A) 100 parts by weight of calcined gypsum, (B) from 0.005 to 5.0 parts by weight of an alkali metal tartrate, (C) from 0.1 to 5.0 parts by weight of a sugar alcohol, and (D) from 0.005 to 3.0 parts by weight of a retarder.

DETAILED DESCRIPTION OF THE INVENTION

While any of conventionally employed calcined gypsum species is employable as component (A), α-type calcined gypsum of extremely high crystallinity which is obtained by dehydration of crystalline gypsum is preferred.

The alkali metal tartrate as component (B) is not particularly limited and includes potassium tartrate, sodium tartrate, potassium sodium tartrate. The alkali metal tartrate is used in an amount of from 0.005 to 5.0 parts by weight, and preferably from 0.02 to 1.0 part by weight, per 100 parts by weight of calcined gypsum. If the amount of the alkali metal tartrate is less than 0.005 part by weight, the coefficient of expansion on setting increases to reduce the dimensional precision. If it exceeds 5.0 parts by weight, the setting time becomes too short, which leads to necessity of addition of a large quantity of a retarder and reduction in smoothness of the resulting gypsum model.

The sugar alcohol as component (C) includes D-arabitol, erythritol, galactitol, D-sorbitol, D-threitol, D-mannitol, and ribitol, with D-sorbitol and D-mannitol being particularly preferred. The sugar alcohol is used in an amount of from 0.1 to 5.0 parts by weight, and preferably from 0.5 to 2.0 parts by weight, per 100 parts by weight of calcined gypsum. If the amount of the sugar alcohol is less than 0.1 part by weight, the effect of improving surface smoothness of the resulting gypsum model cannot be obtained. If it exceeds 5.0 parts by weight, the setting is unfavorably retarded.

The gypsum composition of the present invention contains retarder (compound (D)) for controlling the setting time. The setting time generally ranges from 5 to 30 minutes, and preferably from 5 to 15 minutes. The retarder is added in an amount of from 0.005 to 3.0 parts by weight per 100 parts by weight of the calcined gypsum. Any of known retarders, such as carboxylic acid salts, e.g., citrates, succinates, acetates and malates, borates, e.g., borax, sucrose, hexametaphosphates, ethylenediamine-tetraacetates, starch, gum arabic, and carboxymethyl cellulose, can be used as a retarder.

If desired, the gypsum composition of the present invention may further contain crystalline gypsum for the purpose of setting acceleration. Crystalline gypsum may be added in an amount of from 0.1 to 5.0 parts by weight, and preferably from 0.5 to 2.0 parts by weight, per 100 parts by weight of the calcined gypsum.

If desired, the gypsum composition may furthermore contain other additives, such as pigments, perfumes, and, in some cases, disinfectants or antimicrobial agents. For the purpose of dusting prevention or improvement of preservation stability, it is recommended to add wetting agents or surface active agents to the composition as hereinafter described in detail.

The gypsum composition of the present invention can be prepared by uniformly mixing components (A) to (D) and, if desired, other compounding additives, such as crystalline gypsum, wetting agents, surface active agents, pigments, perfumes, disinfectants, and so on. Uniform mixing can be carried out by means of a high-speed fluid mixer (e.g., a supermixer), a conical screw mixer (e.g., Naughter mixer), a ribbon mixer, a twin-cylinder mixer, and the like. The order of mixing the components is not limited as long as a uniform dispersion may be obtained. For example, all the components may be mixed at once, or the components may be added one after another.

The dental gypsum composition of the present invention is usually supplied in a powdered form. Setting of the gypsum composition is effected by kneading the powder with a prescribed amount of water (called a normal consistency) either manually with a spatula in a rubber-made ball or mechanically by means of a vacuum stirrer. The resulting gypsum slurry is poured into a negative mold, i.e., an impression, and allowed to set in a predetermined time.

In the case of manual kneading, it takes time for the powdered composition to be impregnated and wetted with water so that dusting occurs during kneading with a spatula in a rubber-made ball. Since the dust is irritative and harmful to human giving rise to the hygiene problem, dusting may be reduced by adding a wetting substance containing no water to the gypsum composition to avoid dusting on kneading. Polyhydric alcohols, e.g., ethylene glycol, propylene glycol, glycerin, and ethyl cellosolve are disclosed as the wetting substance containing no water in JP-B-59-17065 (the term "JP-B" as used herein means an "examined published Japanese patent application").

It is also known to add a lipophilic wetting agent in combination with an anionic surface active agent, such as alkylbenzenesulfonates and alkylsulfates, to the powdered gypsum composition as disclosed in JP-A-62-212255 thereby to suppress dusting and also to improve preservation stability. Examples of the alkylbenzenesulfonates include sodium dodecylbenzenesulfonate. Examples of the alkylsulfates include sodium lauryl sulfate, potassium lauryl sulfate, sodium myristyl sulfate, sodium cetyl sulfate, and sodium stearyl sulfate.

It should be noted, however, that the wetting agent or surface active agent added gives influences on the physical and chemical properties of the resulting hardened product. From this viewpoint, the kind and amount thereof should be properly selected as follows.

It is preferable to select the wetting agent(s) to be added in the gypsum composition of the present invention from liquid hydrocarbons, liquid fatty acids, and liquid fatty acid esters. Examples of the liquid hydrocarbons are squalane, liquid paraffin, nonane, decane, and dodecane. Examples of the liquid fatty acids are isostearic acid, oleic acid, linolenic acid, and linoleic acid. Examples of the liquid fatty acid esters are isopropyl myristate, isopropyl palmitate, hexyl laurate, isopropyl isostearate, butyl stearate, ethyl linoleate, isopropyl linoleate, hexyldecyl myristate, hexyldecyl stearate, isostearyl palmitate, hexyldecyl isostearate, octyldodecyl neodecanoate, diethyl sebacate, diisopropyl sebacate, and diisopropyl adipate.

The wetting agent is preferably added in a minimized amount because it causes a reduction in strength of the hardened product. A preferred amount of the wetting agent to be added ranges from 0.5 to 2.0 parts by weight per 100 parts by weight of the calcined gypsum. The level of addition of less than 0.5 part by weight produces little effect on dusting inhibition. The level of addition of more than 2.0 parts by weight causes a considerable reduction in strength of the hardened product.

From the standpoint of obtaining appreciable effects with a minimized amount of the surface active agent, preferred surface active agents to be added together with the wetting agent in the gypsum composition of the present invention are α-olefinsulfonic acid salts, and particularly a sodium or potassium salt of an olefinsulfonic acid having from 14 to 18 carbon atoms. The α-olefinsulfonate is preferably added in an amount of from 0.005 to 0.03 part by weight per 100 parts by weight of the calcined gypsum. If its amount is less than 0.005 part by weight, the oily feeling of the wetting agent cannot be removed. The level of addition exceeding 0.03 part by weight causes a reduction in compatibility with an impression and a reduction in mechanical properties of the hardened product.

The mechanism of action of the gypsum composition according to the present invention in providing a gypsum model excellent in dimensional precision and surface smoothness when combined with an aqueous colloid impression material has not yet been clarified. It is considered that the combination of components (B) to (D), especially components (B) and (C), makes some contribution to control of the setting time of the gypsum composition on the area in contact with an impression.

The present invention is now illustrated in greater detail by way of Examples, but it should be understood that the present invention is not deemed to be limited thereto. All the parts are by weight unless otherwise indicated.

In Examples and Comparative Examples, the normal consistency was so selected as to give a standard viscosity according to the test method of JIS T6505. Measurements of setting time, wet compressive strength, and coefficient of expansion on setting were made in accordance with JIS T6505. The surface roughness of the resulting gypsum model was a centerline average roughness (Ra) as measured with a roughness tester "SURFTEST 401" manufactured by MITUTOYO K. K. according to JIS B0601.

EXAMPLES 1 TO 5 AND COMPARATIVE EXAMPLES 1 AND 2

The components shown in Table 1 below were uniformly mixed to prepare a powdered dental gypsum composition. Water was added thereto at a weight ratio shown in Table 1, and the mixture was kneaded to prepare a sample.

TABLE 1

|  | Example 1 | Example 2 | Example 3 | Example 4 | Example 5 | Compar. Example 1 | Compar. Example 2 |
|---|---|---|---|---|---|---|---|
| Component (part): | | | | | | | |
| Calcined gypsum | 100.00 | 100.00 | 100.00 | 100.00 | 100.00 | 100.00 | 100.0 |
| Retarder* | 0.05 | 0.01 | 0.03 | 0.02 | 0.02 | 0.03 | 0.02 |
| Potassium tartrate | 0.75 | | | | | | |
| Potassium sodium tartrate | | 0.05 | 0.30 | 0.20 | 0.20 | | |
| D-Sorbitol | 2.00 | | | 1.00 | 1.00 | | |
| D-Mannitol | | 0.80 | 2.00 | | | | |
| Crystalline gypsum | | | 1.00 | | 1.00 | | |
| Potassium sulfate | | | | | | 0.30 | |
| Resin** | | | | | | | 0.50 |
| Water/Gypsum Composition Weight Ratio | 0.23 | 0.24 | 0.24 | 0.23 | 0.23 | 0.25 | 0.20 |

Note: *: Sodium citrate
**: Sulfonated melamine-formaldehyde condensate

The setting time, the wet compressive strength after 3 hours, and the coefficient of expansion after 2 hours were measured. The results obtained are shown in Table 2 below.

An impression patterned on a polyester film surface was prepared by using each of (a) an alginate-based impression material ("AROMAFINE" produced by G. C. Co., Ltd.), (b) an agar-based impression material ("M-LOID" produced by Dentrochemical Co., Ltd.), and (c) an agar-based impression material ("HYDROSTICK" produced by Omnico Co., Ltd.). The sample was cast onto the surface of the impression and allowed to stand at room temperature for 60 minutes. After setting, the gypsum was removed from the impression and further allowed to stand for 24 hours. The surface roughness of the gypsum on the surface having contacted with the impression was measured. The result obtained is also shown in Table 2.

EXAMPLES 6 TO 9 AND COMPARATIVE EXAMPLES 3 TO 5

The components shown in Table 3 below were uniformly mixed to prepare a powdered dental gypsum composition. The amount of dust of the resulting powder was directly measured by using "Digital Dust Indicator" ("SHIBATA P-5LII" manufactured by Shibata Kagaku Kikai Kogyo K.K.). The results obtained are shown in Table 4 below.

Water was added to the composition at a weight ratio shown in Table 3, and the mixture was kneaded to prepare a sample.

TABLE 2

|  | Example 1 | Example 2 | Example 3 | Example 4 | Example 5 | Compar. Example 1 | Compar. Example 2 |
|---|---|---|---|---|---|---|---|
| Setting Time (min) | 9.8 | 10.2 | 10.1 | 9.9 | 10.0 | 10.0 | 10.5 |
| Wet Compressive Strength (after 3 hrs) (kg/cm$^2$) | 585 | 575 | 570 | 580 | 590 | 420 | 670 |
| Coefficient of Expansion on Setting (after 2 hrs) (%) | 0.20 | 0.21 | 0.20 | 0.21 | 0.19 | 0.30 | 0.20 |
| Surface Roughness (Ra) of Hardened Product (μm): | | | | | | | |
| Impression A | 1.3 | 1.1 | 1.1 | 1.1 | 1.1 | 1.6 | 2.1 |
| Impression B | 1.0 | 1.0 | 0.9 | 0.9 | 0.8 | 1.8 | 1.2 |
| Impression C | 2.6 | 2.1 | 1.9 | 1.8 | 1.5 | 8.5 | 9.3 |

It can be apparently seen from the results in Table 2 that the gypsum composition according to the present invention exhibits excellent compatibility with agar impression materials.

TABLE 3

|  | Example 6 | Example 7 | Example 8 | Example 9 | Compar. Example 3 | Compar. Example 4 | Compar. Example 5 |
|---|---|---|---|---|---|---|---|
| Component (part): | | | | | | | |
| Calcined gypsum | 100.00 | 100.00 | 100.00 | 100.00 | 100.00 | 100.00 | 100.00 |
| Sodium citrate | 0.02 | 0.03 | 0.03 | 0.02 | 0.03 | 0.03 | 0.03 |
| Potassium sodium tartrate | 0.30 | 0.30 | | 0.20 | | | |

TABLE 3-continued

|  | Example 6 | Example 7 | Example 8 | Example 9 | Compar. Example 3 | Compar. Example 4 | Compar. Example 5 |
|---|---|---|---|---|---|---|---|
| Potassium tartrate |  |  | 0.30 |  |  |  |  |
| D-Sorbitol | 1.00 | 1.00 |  | 1.00 |  |  |  |
| D-Mannitol |  |  | 2.00 |  |  |  |  |
| Crystalline Gypsum |  |  |  | 1.00 |  |  |  |
| Sulfonated melamine-formaldehyde condensate |  |  |  |  | 0.50 | 0.50 | 0.50 |
| Squalane |  | 1.00 |  |  |  | 2.00 |  |
| Liquid paraffin |  |  | 1.00 | 1.0 |  |  |  |
| Sodium α-olefinsulfonate |  | 0.01 | 0.01 | 0.01 |  |  |  |
| Potassium sulfate |  |  |  |  | 0.30 | 0.30 | 0.30 |
| Sodium laurylsulfate |  |  |  |  |  | 0.40 |  |
| Isopropyl isostearate |  |  |  |  |  |  | 2.60 |
| Sodium dodecylbenzene-sulfonate |  |  |  |  |  |  | 0.40 |
| Water/Gypsum Composition Weight Ratio | 0.23 | 0.23 | 0.23 | 0.23 | 0.24 | 0.24 | 0.24 |

The setting time, the wet compressive strength after 3 hours, and the coefficient of expansion after 2 hours were measured. The results obtained are shown in Table 4 below.

An impression patterned on a polyester film surface was made by using the same agar-based impression material (B) or (C) as used in Example 1. The sample was cast on the surface of the impression and allowed to stand at room temperature for 60 minutes. After setting, the gypsum was removed from the impression and further allowed to stand for 24 hours. The surface roughness of the gypsum on the surface having contacted with the impression was measured. The result obtained is also shown in Table 4.

TABLE 4

|  | Example 6 | Example 7 | Example 8 | Example 9 | Compar. Example 3 | Compar. Example 4 | Compar. Example 5 |
|---|---|---|---|---|---|---|---|
| Setting Time (min) | 10.3 | 10.1 | 10.2 | 10.0 | 10.3 | 11.8 | 12.3 |
| Wet Compressive Strength (after 3 hrs) (kg/cm$^2$) | 555 | 550 | 545 | 550 | 570 | 510 | 505 |
| Coefficient of Expansion on Setting (after 2 hrs) (%) | 0.16 | 0.16 | 0.15 | 0.16 | 0.22 | 0.24 | 0.24 |
| Surface Roughness (Ra) of Hardened Product (μm): |  |  |  |  |  |  |  |
| Impression B | 1.0 | 1.1 | 1.1 | 1.0 | 1.2 | 1.3 | 1.8 |
| Impression C | 1.9 | 2.0 | 2.7 | 1.8 | 8.5 | 8.8 | 7.8 |
| Amount of Dust (mg/m$^3$) | 25.6 | 1.8 | 1.9 | 1.8 | 38.7 | 2.2 | 2.4 |

As described above, the dental gypsum composition of the present invention provides a denture model having a smooth surface with excellent dimensional precision and excellent mechanical strength even when combined with aqueous colloidal impression materials, such as agar materials or alginate materials as well as rubber impression materials.

While the invention has been described in detail and with reference to specific examples thereof, it will be apparent to one skilled in the art that various changes and modifications can be made therein without departing from the spirit and scope thereof.

What is claimed is:

1. A composition for a dental gypsum model consisting essentially of (A) 100 parts by weight of α-type calcined gypsum, (B) from 0.005 to 5.0 parts by weight of an alkali metal tartrate, (C) from 0.1 to 5.0 parts by weight of a sugar alcohol, (D) from 0.005 to 3.0 parts by weight of a retarder and (G) from 0.1 to 5.0 parts by weight of a setting accelerator.

2. A composition for a dental gypsum model as claimed in claim 1, wherein said sugar alcohol is D-sorbitol or D-mannitol.

3. A composition for a dental gypsum model as claimed in claim 1, wherein said setting accelerator is crystalline gypsum.

4. A composition for a dental gypsum model consisting essentially of (A) 100 parts by weight of α-type calcined gypsum, (B) from 0.005 to 5.0 parts by weight of an alkali metal tartrate, (C) from 0.1 to 5.0 parts by weight of a sugar alcohol, (D) from 0.005 to 3.0 parts by weight of a retarder, (E) from 0.5 to 2.0 parts by weight of a wetting agent, and (F) from 0.005 to 0.03 part by weight of an α-olefinsulfonic acid salt.

5. A composition for a dental gypsum model as claimed in claim 4, wherein said sugar alcohol is D-sorbitol or D-mannitol.

6. A composition for a dental gypsum model as claimed in claim 4, wherein said wetting agent is selected from the group consisting of liquid hydrocarbons, liquid fatty acids, and liquid fatty acid esters.

7. A composition for a dental gypsum model as claimed in claim 4, wherein said composition further consists essentially of (G) from 0.1 to 5.0 parts by weight of a setting accelerator.

8. A composition for a dental gypsum model as claimed in claim 4, wherein said setting accelerator is crystalline gypsum.

* * * * *